(12) United States Patent
Zantl et al.

(10) Patent No.: US 8,263,391 B2
(45) Date of Patent: Sep. 11, 2012

(54) SPECIMEN CARRIER FOR THE STUDY OF CELL GROWTH

(75) Inventors: Roman Zantl, Baidham (DE); Valentin Kahl, München (DE)

(73) Assignee: ibidi GmbH, Martinsried (DE)

( * ) Notice: Subject to any disclaimer, the term of this patent is extended or adjusted under 35 U.S.C. 154(b) by 1431 days.

(21) Appl. No.: 11/779,978

(22) Filed: Jul. 19, 2007

(65) Prior Publication Data

US 2008/0020455 A1  Jan. 24, 2008

(30) Foreign Application Priority Data

Jul. 20, 2006 (EP) ..................... 06015167

(51) Int. Cl.
*C12M 1/34* (2006.01)
*C12M 3/00* (2006.01)

(52) U.S. Cl. ............... 435/288.3; 435/289.1; 435/305.1; 422/500; 422/503; 422/551; 436/165; 356/246

(58) Field of Classification Search ............... 435/288.3, 435/289.1, 305.1; 422/500, 503, 551; 436/165; 356/246

See application file for complete search history.

(56) References Cited

U.S. PATENT DOCUMENTS

| | | | | |
|---|---|---|---|---|
| 4,254,223 A | * | 3/1981 | Schuurs et al. | 435/287.2 |
| 4,741,619 A | * | 5/1988 | Humphries et al. | 356/246 |
| 4,912,037 A | * | 3/1990 | Lemonnier | 435/34 |
| 5,180,555 A | * | 1/1993 | Monget | 422/552 |
| 5,229,163 A | | 7/1993 | Fox | |
| 5,792,654 A | * | 8/1998 | Bohannon et al. | 435/305.3 |
| 6,312,952 B1 | | 11/2001 | Hicks | |
| 7,233,391 B2 | * | 6/2007 | Schermer et al. | 356/246 |
| 2005/0101010 A1 | * | 5/2005 | Li | 435/304.3 |

FOREIGN PATENT DOCUMENTS

| | | |
|---|---|---|
| EP | 1079224 A2 | 2/2001 |
| EP | 1609851 A | 12/2005 |
| WO | 2003036265 A2 | 5/2003 |
| WO | 2004071661 A | 8/2004 |

* cited by examiner

*Primary Examiner* — William H Beisner
*Assistant Examiner* — Danielle Henkel
(74) *Attorney, Agent, or Firm* — IP Strategies

(57) ABSTRACT

The invention relates to a specimen carrier for the study of cell growth, comprising a substrate with a reservoir with a bottom, wherein the reservoir is filled up to a predetermined height of the side wall, which is smaller than the complete height of the reservoir, with a carrier material for cell growth and the side wall of the reservoir is formed such that a predetermined contact angle of the carrier material can be adjusted with respect to the side wall.

19 Claims, 3 Drawing Sheets

SPECIMEN CARRIER FOR THE STUDY OF CELL GROWTH

FIELD OF THE INVENTION

The invention relates to a specimen carrier for the study of cell growth, in particular for angiogenesis studies.

BACKGROUND OF THE INVENTION

In cell biology cell growth examinations are often carried out in that a carrier material, such as for example, a collagen gel such as the BD Matrigel from Becton, Dickinson and Company is placed into indentations on 96-well, 48-well or 24-well plates. This type of carrier material is generally also known as a matrix.

On a matrix of this nature for example cells which form blood vessels, e.g. Human Umbilical Vein Endothelial Cells (HUVEC), are then distributed. After a certain time (e.g. hours or days) the cells then indicate a characteristic, mesh-type structure, which shows that the cells are able to form, for example blood vessels. The cell structures are then, for example, examined with microscopes, preferably with phase contrast.

Examinations of this nature are in particular used in tumour research, wherein the objective is to inhibit the formation of new blood vessels through pharmacological and biotechnological methods and substances, thus preventing tumour growth. Since tumours, due to their strong growth, have a very high requirement of blood gases and nutrients, their growth is especially dependent on a good supply of these. Therefore, cell growth can be restricted by preventing the blood vessel formation.

If during cell growth examinations the indentations in conventional well plates are partly filled with appropriate carrier materials, a surface of the carrier material is obtained at a corresponding level of each of the indentations. Due to surface tension effects the shape of the surface cannot be determined beforehand. Since the growth of the cells then placed in a culture medium is affected by the surface geometry of the carrier material, it takes place uncontrollably. The unknown surface geometry and the uncontrolled cell growth also make the following microscopic examinations more difficult.

BRIEF SUMMARY OF THE INVENTION

In view of this disadvantage of the state of the art it is therefore the object of the invention to provide a specimen carrier for the examination of cell growth, which facilitates a better controlled cell growth and that the ensuing microscopic examinations can be carried out with higher accuracy and flexibility. This object is solved by the subject matter of Claim 1.

According to the invention, a specimen carrier for the examination of cell growth is provided, comprising
 a substrate with a reservoir with a bottom,
 wherein the reservoir is filled up to a predetermined height of the side wall, which is lower than the overall height of the reservoir, with a carrier material for cell growth, and
 the side wall of the reservoir is formed such that a predetermined contact angle of the carrier material can be adjusted with respect to the side wall.

Due to the adjustability of the contact angle, i.e. of the angle between the side wall and the surface of the carrier material, a choice can be made of whether and in which thickness the carrier material forms a meniscus. Thus the surface geometry can be accurately adjusted. This in particular facilitates the adjustment of a contact angle of 90° so that the carrier material exhibits a planar surface. Also contact angles greater than 90° are possible in order to obtain a carrier material surface which curves upwards. For some examinations it can be of advantage to adjust the contact angle to about 90°, because in this case the cells to be examined grow in a plane which facilitates high microscopic magnification with a small depth of focus. On the other hand, for some examinations a meniscus with a contact angle smaller than 90° is required, because then cells added to the culture medium collect at the deepest point of the carrier material. A very flexible and accurate adaptation of the surface geometry to the following examinations to be carried out is thus possible.

The adjustability of the contact angle also has the advantage that the amount of the carrier material used can be precisely dosed. If in particular the carrier material must have a minimum thickness for certain examinations, in the case of a meniscus formation unnecessary carrier material is made available at the side walls.

With a formation of the side wall of this nature the contact angle of an added culture medium, in particular based on water, can also be adjusted. Thus, the situation can be obtained, for example, in which the carrier material has the required meniscus, but the culture medium however has a contact angle of 90° and therefore a plane surface. Particularly with slight differences of refractive index of carrier material and culture medium, in this way easy microscope observation over the whole area occupied by cells can be ensured. In particular it is of advantage if boundary areas with relevant differences of refractive index (for example with a difference of at least 0.2) are located in the optical path of a microscope perpendicular to the optical axis. If the carrier material differs appropriately in its refractive index compared to the culture medium positioned above it, a contact angle of about 90° is also advantageously chosen for the carrier material.

The side wall of the reservoir can have an edge at a predetermined height, in particular a circumferential edge, such that the predetermined contact angle of the carrier material can be adjusted with respect to the side wall. The edge can in particular be formed by a protrusion. With an edge at the predetermined height, the contact angle is to be determined with reference to the side wall below the edge, i.e. between the bottom and the edge.

Due to the edge, the contact angle can be adjusted to the predetermined height. If, in particular during filling with the carrier material, a meniscus forms, then this meniscus remains present as long as the carrier material at the sides has not yet reached the edge. Once the edge is reached and further carrier material is added, the carrier material at the side walls does not rise further due to the surface tension at the edge; instead if the contact angle increases or the meniscus reduces with further addition of carrier material, the contact angle can be increased to over 90° as long as the surface tension of the carrier material prevents the carrier material rising at the side walls above the edge and the predetermined height.

The side wall of the reservoir can have at the predetermined height a shoulder, in particular a circumferential shoulder, wherein the reservoir, parallel to the bottom, has a first cross-sectional area immediately below the predetermined height and a second cross-sectional area immediately above the predetermined height, wherein the second cross-sectional area is larger than the first cross-sectional area.

A right-angled edge, for example, can be formed by a shoulder. The shoulder facilitates the adjustment of the contact angle of the carrier material, because, due to the edge at the shoulder, the carrier material initially does not rise further due to the surface tension on reaching the shoulder on the side wall, but rather the meniscus is reduced.

In principle the sections of the reservoir below and above the predetermined height can take any and various shapes. They can, for example, be formed conically.

In particular, the reservoir can have in parallel to the bottom a first cross-sectional area from the bottom to the predetermined height and from the predetermined height up to a further predetermined height a second cross-sectional area, wherein the second cross-sectional area is larger than the first cross-sectional area.

Thus, both sections of the reservoir (between the bottom and the (first) predetermined height and between the (first) predetermined height and the other predetermined height) are formed cylindrically. The shoulder formed in this way has a right-angled edge. The cross-sectional area can here be formed, for example, with a circular or rectangular shape. With these embodiments the further predetermined height need not correspond to the complete height of the reservoir.

With the previously described specimen carriers the size ratio of the second to the first cross-sectional area can be at least 1.2, preferably at least 1.8, more preferably 2-4. With these size ratios an edge is formed in a particularly advantageous manner, which facilitates the adjustment of a predetermined contact angle during the filling of the reservoir up to the (first) predetermined height.

In particular, the first cross-sectional area can have an area of $0.8\ mm^2$-$175\ mm^2$, preferably $0.8$-$65\ mm^2$. The first and/or second cross-sectional area can be formed elliptically or circular. Through the lack of edges running to the bottom, the dead volume is reduced and unwanted surface tension effects are avoided.

With the specimen carriers previously described the predetermined height can be 50 μm-1 mm, preferably 50-250 μm. A carrier material with such a range of thickness facilitates in an advantageous way the growth of distributed cells and provides good observation by means of microscopic methods.

The bottom of the specimen carriers previously described can have a thickness of 1 μm-2 mm, preferably 10 μm-250 μm. Thus, in particular examinations by means of inverse microscopy are possible.

The bottom of the specimen carriers previously described can comprise an optically transparent material, in particular glass or a plastic, such as COC (cyclo-olefin copolymer), COP (cyclo-olefin polymer), PMMA (polymethylmethacrylate), PC (polycarbonate), PE (polyethylene) or PS (polystyrene).

The specimen carrier can be manufactured in a simple manner with these materials and then used for inverse microscopy. With the specimen carriers previously described the bottom can essentially exhibit no autofluorescence for visible light and/or a refractive index greater than 1.2 and/or smaller than 1.7.

Essentially no autofluorescence means that the autofluorescence is smaller or equal to the autofluorescence of a conventional cover slip (for example pure white glass of the hydrolytic class 1, such as Menzel cover slips, in particular in the thickness no. 1.5). Optical characteristics of this nature are in particular a big advantage with inverse microscopy.

With the specimen carriers described above the carrier material can comprise a gel, in particular a cross-linked or polymerised gel, silicone or a polymer, in particular a cross-linked polymer. These materials are in a particularly advantageous manner suitable for the growth of cells in their surface.

With the previously described specimen carriers the predetermined contact angle can be adjusted such that the difference between the contact angle and the slope angle of the side wall with respect to the bottom is −45° to +45°, preferably −20° to +20°, further preferably −10° to +10°, in particular 0°.

With a side wall standing perpendicular to the bottom between the bottom and the predetermined height a difference of 0° between the contact angle and the slope angle signifies that the surface of the carrier material is planar and runs parallel to the bottom. If the difference is negative, a meniscus is formed, whereas with a positive difference the carrier material is curved upwards.

Depending on the type of examination to be carried out, a different choice of the contact angle may be of advantage. With a planar surface of the carrier material parallel to the bottom, disseminated cells will essentially grow in one plane so that here microscopy and examinations at high magnification and low depth of focus are possible. The formation of a meniscus can be desirable when the cells in particular during dissemination are to collect in a small area about the lowest point of the surface of the carrier material.

With the adjustment of the contact angle it must furthermore be considered that boundary areas with significant differences of refractive index can be advantageously arranged perpendicular to the optical path of a microscope or parallel to the bottom of the reservoir. A difference in refractive index is in particular significant when it is greater than 0.2, especially greater than 0.3. Thus a difference of 0° between the contact angle and the slope angle, in particular with the use of carrier materials which exhibit a significant difference in refractive index to the culture medium, is advantageous, because then the boundary area between the carrier material and the culture medium is formed parallel to the bottom and perpendicular to the optical axis.

With the previously described specimen carriers the side wall on predetermined regions can be formed hydrophilically and/or hydrophobically. In this way it is also possible to adjust or influence the contact angle. Hydrophilic or hydrophobic regions can for example be produced by suitable coatings or surface treatments.

The substrate of the previously described specimen carriers can comprise a plastic. In particular with the previously described specimen carriers the substrate can comprise a plastic film which forms the bottom of the reservoir. The substrate can in particular comprise just one plastic.

Alternatively, the substrate of the previously described specimen carriers can be formed in one piece, in particular as an injection moulded part. Thus the specimen carrier can be produced in a particularly simple manner.

The previously described specimen carriers can also comprise a lid for closing off the reservoir. The surface facing the reservoir and/or the surface of the lid facing away from the reservoir can be formed here in particular planar and parallel to the bottom of the reservoir. This enables the boundary area of the lid to air or to a culture medium introduced into the reservoir to be aligned perpendicular to an optical axis.

BRIEF DESCRIPTION OF THE DRAWINGS

Further advantages and features of the invention are explained in the following based on the figures. The following are illustrated.

DETAILED DESCRIPTION OF THE INVENTION

Figure 1:
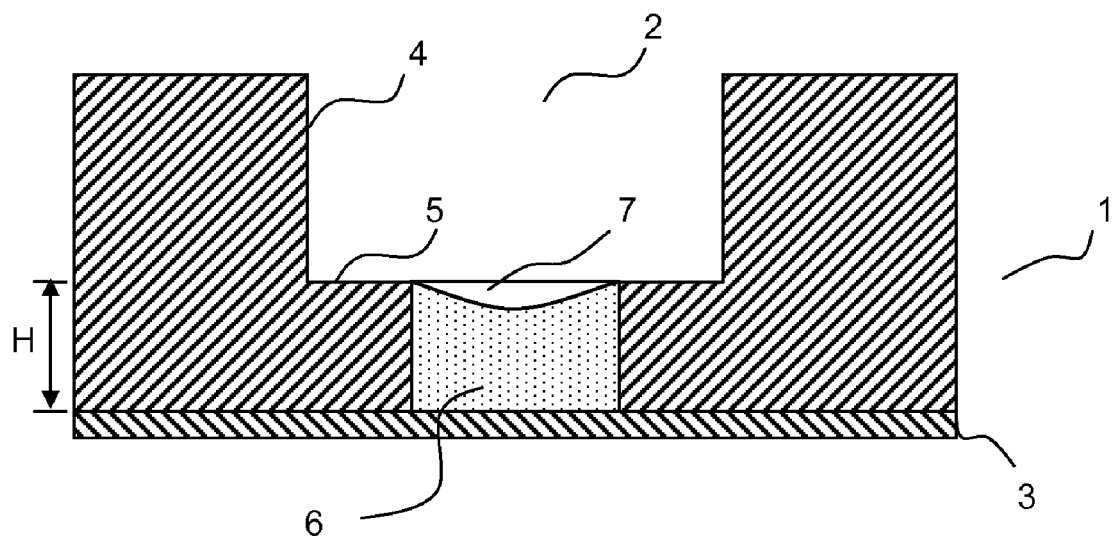
FIG. 1 a specimen carrier, formed in two parts, with which the carrier material and the culture medium are filled to the predetermined height.

FIG. 1 schematically illustrates a specimen carrier with a substrate 1 in cross-section, wherein a reservoir 2 is formed in the substrate 1. The substrate 1 comprises a plastic film 3 which forms the bottom of the reservoir 2. The reservoir has two cylindrical sections. The first section extends from the bottom up to a predetermined height H. At this height the side wall 4 of the reservoir has a shoulder 5 which forms a circumferential right-angled edge. The second section of the reservoir extends from the predetermined height H to the total height of the reservoir.

In the illustrated embodiment the cross-sectional area of the first section up to the height H is smaller than the cross-sectional area of the second section immediately above the predetermined height H.

The first section of the reservoir is filled up to the predetermined height H with a carrier material 6, i.e. the carrier material extends at its highest point (on the side wall) up to the height H. The carrier material may be, for example, a collagen gel such as the product BD Matrigel from Becton, Dickinson and Company.

The edge formed by the shoulder at the height H enables the contact angle of the carrier material 6 to be adjusted with respect to the side wall 4. On filling the first section with the carrier material, first of all a meniscus is formed. This remains present until the carrier material has reached the height H on the side wall. At the edge of the protrusion the carrier material does not rise any more on further filling due to the surface tension; instead the contact angle reduces and thus also the meniscus. In the illustrated example the contact angle with respect to the side wall is smaller than 90°; this means that the difference between the contact angle and the slope angle of the side wall with respect to the bottom, wherein the slope angle in the illustrated example is 90°, is negative.

The carrier material is normally filled in liquid form and then hardens. Hardening can be accelerated for example by heating the carrier material. Thus, the carrier material is prevented after filling, where applicable, from creeping over the edge of the shoulder during hardening.

A culture medium 7, containing cells, is placed in the indentation formed by the meniscus of the carrier material 6. Also in the case of filling with culture medium, it initially forms a meniscus, which on further filling reduces to the edge of the shoulder so that, as in the illustrated example, a contact angle of the culture medium of 90° can be adjusted with respect to the side wall. Thus the boundary area between the culture medium 7 and the air is planar and parallel to the bottom. It is in particular also perpendicular to the optical axis when carrying out an examination by means of inverse microscopy.

The illustrated configuration is particularly advantageous when the difference in the refractive index between the carrier material 6 and the culture medium 7 is small, for example smaller than 0.2, so that primarily the boundary areas between the culture medium and the air or between the carrier material and the reservoir bottom are important for the microscopic examination. However, it must be taken into account that with the formation of a meniscus by the carrier material, the cells do not grow in one plane so that with a microscopic examination an adequate depth of focus must be made available.

In particular with examinations by means of inverse microscopy it is necessary that the bottom 3 is optically transparent and optionally exhibits further predetermined optical characteristics, such as for example a low autofluorescence. Furthermore, also a low bottom thickness is advantageous for microscopic examinations. This can in particular be achieved in that the bottom is formed by a plastic film, for example with a thickness between 10 and 250 µm, which is joined to the other part of the substrate, for example by gluing or ultrasonic bonding.

Figure 2:
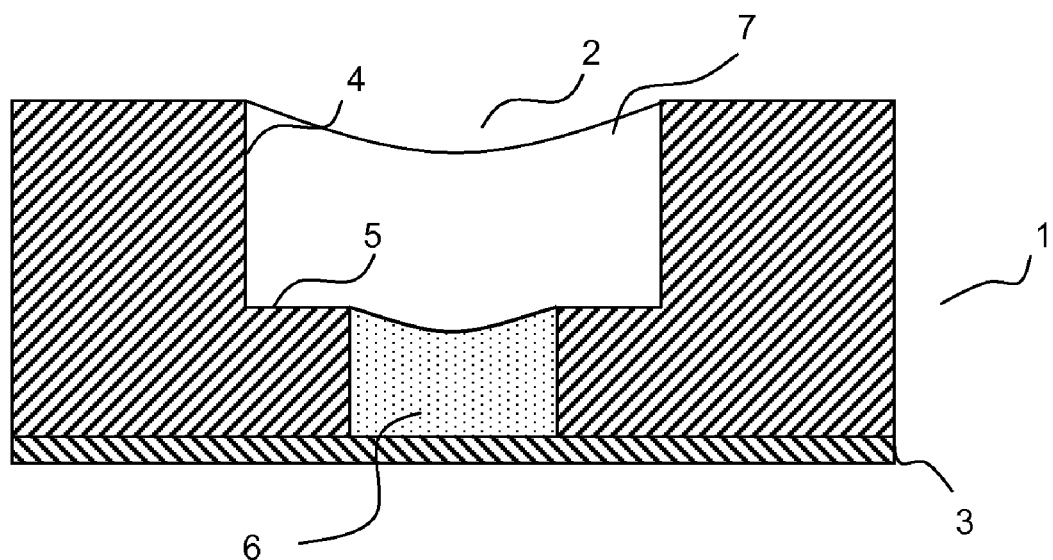
FIG. 2 a specimen carrier, formed in two parts, with which a culture medium is filled up to the total height of the reservoir.

The reservoir geometry illustrated in FIG. 1 with two sections of different cross-sectional area has the further advantage that also larger amounts of culture medium can be added without it overflowing uncontrollably and contaminating the specimen carrier. A case with a large amount of culture medium is illustrated schematically in the cross-sectional view in FIG. 2. Here, the culture medium 7 has been filled to the total height of the reservoir, wherein in the illustrated example a meniscus is still present in the culture medium.

The specimen carrier can furthermore comprise a lid which is fitted to the substrate and closes off the reservoir.

Figure 3:
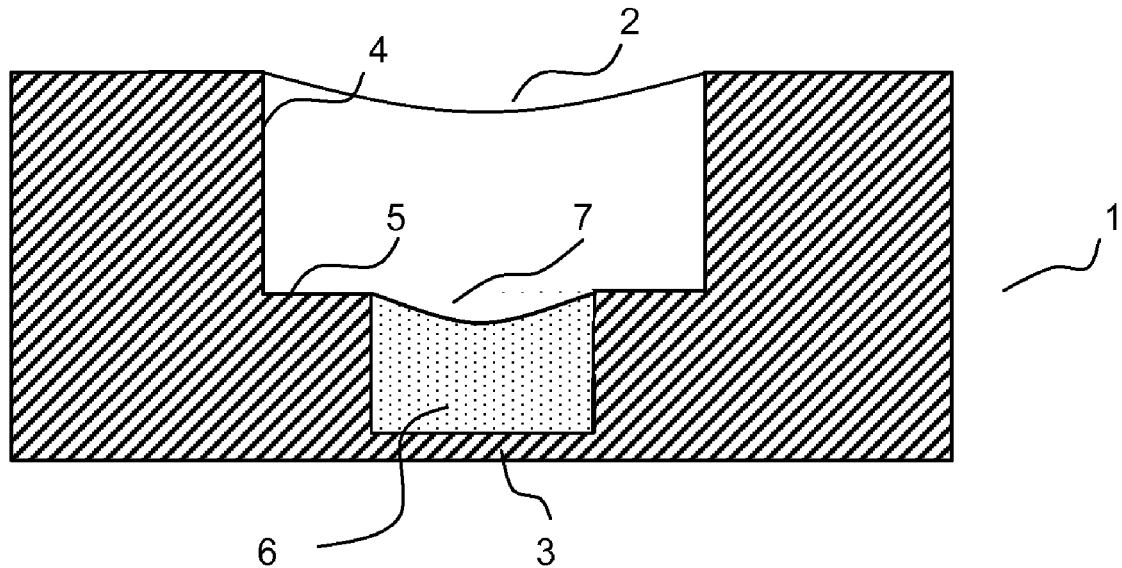
FIG. 3 a one-part specimen carrier, with which the carrier material has a surface parallel to the reservoir bottom.

In FIG. 3 a schematic cross-sectional view of a substrate 1 of a specimen carrier is shown formed as one piece. The reservoir geometry corresponds to the shape illustrated in FIGS. 1 and 2. In FIG. 3 the carrier material 6 has however been filled up to the shoulder such that the contact angle with respect to the side wall is 90° or the difference between the contact angle and the slope angle of the side wall is 0°. In this way the surface of the carrier material has been set planar. This has in particular the advantage that disseminated cells grow on the carrier material in one plane so that no particularly large depth of focus is required during microscopic examinations. Due to the second section of the reservoir above the predetermined height, despite the planar carrier material surface, a large amount of culture medium can be added with cells to be examined.

The one-part substrate can in particular be an injection moulded part which facilitates easy manufacture.

Figure 4:
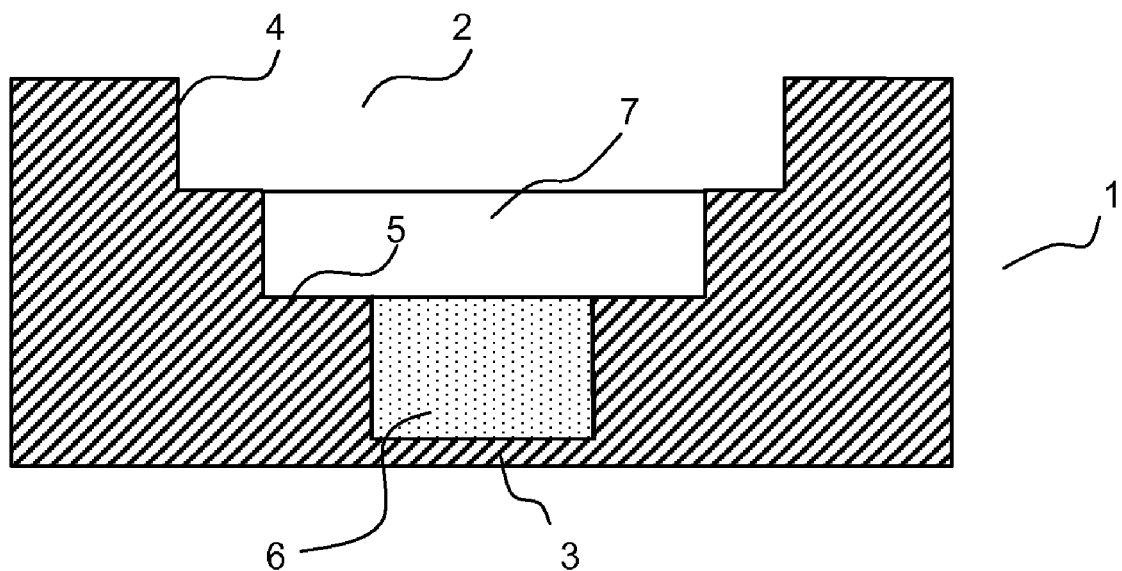
FIG. 4 a one-part specimen carrier, in which the culture medium is filled to above the predetermined height, but not up to the total height of the reservoir.

In FIG. 4 a further embodiment of a one-part substrate 1 of a specimen carrier is illustrated. In this example the reservoir has three sections; a first one, which extends up to the predetermined height to which the carrier material is filled, a second section up to a further predetermined height, as well as a third section up to the total height of the reservoir.

The cross-sectional areas increase from section to section, wherein each section is formed cylindrically so that at the (first) predetermined height and at the further predetermined height a shoulder is formed which facilitates the adjustment of a predetermined contact angle at the respective edge. Here, the contact angle of the carrier material is adjusted to the first predetermined height and the contact angle of the culture medium is adjusted to the further predetermined height, with respect to the side wall in each case.

The third section between the further predetermined height and the total height of the reservoir prevents the complete specimen carrier from being contaminated when the culture medium overflows. In the example illustrated in FIG. 4 the contact angles of the carrier material and the culture medium are adjusted such that the boundary areas between the carrier material and the culture medium or between the culture medium and the air are formed planar and parallel to the bottom.

Figure 5:
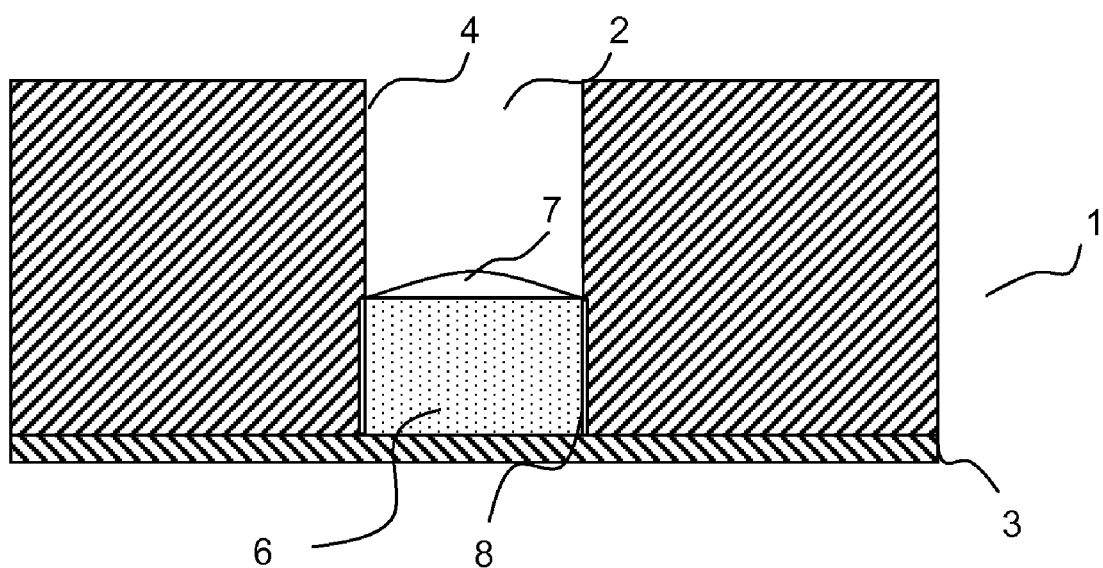
FIG. 5 a specimen carrier, formed in two parts, with a partially hydrophilised surface.

FIG. 5 schematically illustrates a further embodiment in which the side wall 4 has a hydrophilic region 8 up to the predetermined height H. This region can, for example, be obtained by a plasma treatment in which the upper section of the side wall 4 which is not to be treated is covered up. A hydrophilic section 8 of this nature also facilitates the filling of the reservoir 2 up to the predetermined height H with carrier material such that the contact angle is 90°. In the illustrated example the contact angle between the culture medium 7 and the side wall 4 is more than 90°.

The features quoted in the previously explained examples can however also be combined in other ways.

What is claimed is:

1. Specimen carrier for the study of cell growth, comprising:
    a substrate having a reservoir with a bottom and a side wall, wherein the sidewall is lower than an overall height of the reservoir, and
    a carrier material for cell growth,
    wherein the reservoir is filled up to a predetermined height of the side wall with the carrier material,
    wherein the side wall of the reservoir has a circumferential shoulder at said predetermined height, wherein the circumferential shoulder is arranged substantially perpendicularly to an upper edge of the side wall, and wherein a predetermined contact angle of the carrier material is arranged with respect to the side wall so that the carrier material exhibits a planar surface, and
    wherein the carrier material is a hardened liquid material.

2. Specimen carrier according to claim 1, wherein the reservoir has parallel to the bottom a first cross-sectional area immediately below the predetermined height and a second cross-sectional area immediately above the predetermined height, wherein the second cross-sectional area is larger than the first cross-sectional area.

3. Specimen carrier according to claim 1, wherein the reservoir has parallel to the bottom a first cross-sectional area from the bottom to the predetermined height and from the predetermined height up to a further predetermined height a second cross-sectional area, wherein the second cross-sectional area is larger than the first cross-sectional area.

4. Specimen carrier according to claim 2, wherein the size ratio of the second to the first cross-sectional area is at least 1.2.

5. Specimen carrier according to claim 2, wherein the first cross-sectional area has an area of 0.8-175 mm$^2$.

6. Specimen carrier according to claim 1, wherein the predetermined height is 50 μm-1 mm.

7. Specimen carrier according to claim 1, wherein the bottom has a thickness from 1 μm to 2 mm.

8. Specimen carrier according to claim 1, wherein the bottom comprises an optically transparent material.

9. Specimen carrier according to claim 1, wherein the bottom exhibits essentially no autofluorescence for visible light and/or a refractive index greater than 1.2 and or smaller than 1.7.

10. Specimen carrier according to claim 1, wherein the carrier material comprises a gel, silicone or a polymer.

11. Specimen carrier according to claim 1, wherein the predetermined contact angle can be adjusted such that the difference between the contact angle and the slope angle of the side wall with respect to the bottom is −45° to +45°.

12. Specimen carrier according to claim 1, wherein the side wall at predetermined regions is formed hydrophilically and/or hydrophobically.

13. Specimen carrier according to claim 1, wherein the substrate comprises a plastic.

14. Specimen carrier according to claim 1, wherein the substrate comprises a plastic film which forms the bottom of the reservoir.

15. Specimen carrier according to claim 1, wherein the substrate is formed from one piece.

16. Specimen carrier according to claim 1, wherein the predetermined contact angle is substantially 90 degrees.

17. Specimen carrier according to claim 1, wherein the edge defines a surface outside of the side wall and at an edge angle with respect to the side wall.

18. Specimen carrier according to claim 17, wherein the edge angle is substantially 90 degrees.

19. Method for studying cell growth, comprising:
    providing a specimen carrier comprising a substrate with a reservoir with a bottom and a side wall,
    filling the reservoir up to a predetermined height of the side wall, which is lower than the overall height of the reservoir, with a carrier material for cell growth, wherein the side wall of the reservoir has a circumferential shoulder at said predetermined height such that a predetermined contact angle of the carrier material is adjusted with respect to the side wall so that the carrier material exhibits a planar surface, and wherein the carrier material is a hardened liquid material, and
    disseminating cells on the planar surface of the carrier material.

* * * * *